(12) United States Patent
Nguyen et al.

(10) Patent No.: US 9,855,437 B2
(45) Date of Patent: Jan. 2, 2018

(54) HINGED RESONANT POWER TRANSFER COIL

(71) Applicant: TC1 LLC, Pleasanton, CA (US)

(72) Inventors: John Duc Nguyen, San Ramon, CA (US); Carine Hoarau, Lafayette, CA (US); Stephen Zimmermann, Fremont, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/032,293

(22) PCT Filed: Nov. 11, 2014

(86) PCT No.: PCT/US2014/064959
§ 371 (c)(1),
(2) Date: Apr. 26, 2016

(87) PCT Pub. No.: WO2015/070202
PCT Pub. Date: May 14, 2015

(65) Prior Publication Data
US 2016/0250484 A1 Sep. 1, 2016

Related U.S. Application Data

(60) Provisional application No. 61/902,694, filed on Nov. 11, 2013.

(51) Int. Cl.
*A61N 1/00* (2006.01)
*A61N 1/378* (2006.01)
(Continued)

(52) U.S. Cl.
CPC ....... *A61N 1/3787* (2013.01); *A61N 1/37229* (2013.01); *H02J 50/12* (2016.02)

(58) Field of Classification Search
CPC ... A61N 1/3787; A61N 1/37229; H02J 50/00; H02J 50/05; H02J 50/10; H02J 50/12
See application file for complete search history.

(56) References Cited

U.S. PATENT DOCUMENTS

| 4,041,955 A | 8/1977 | Kelly et al. |
|---|---|---|
| 4,352,960 A | 10/1982 | Dormer et al. |

(Continued)

FOREIGN PATENT DOCUMENTS

| DE | 202012000166 U1 | 6/2013 |
|---|---|---|
| DE | 102012201073 A1 | 7/2013 |

(Continued)

OTHER PUBLICATIONS

International Search Report and Written Opinion issued in PCT/US2014/064959 dated May 12, 2015.

(Continued)

*Primary Examiner* — Scott Getzow
(74) *Attorney, Agent, or Firm* — Armstrong Teasdale LLP

(57) ABSTRACT

Methods and apparatus for wireless power transfer and communications are provided. In one embodiment, a resonator of a wireless power transfer system comprises a plurality of links connected to another with hinges to form a coil housing, the coil housing being adjustable at the hinges to conform to a body of a patient, and a flexible conductor wire attached to the coil housing, the flexible conductor wire being configured to transmit or receive wireless power. The resonator can be infinitely adjusted at the hinges to conform the shape of the resonator to a patient's body. In some embodiments, a locking mechanism can be configured to lock the resonator into a preferred position.

20 Claims, 8 Drawing Sheets

(51) Int. Cl.
*H02J 50/12* (2016.01)
*A61N 1/372* (2006.01)

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | LaFranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler, Jr. et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbanaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,079,043 B2* | 7/2015 | Stark .................. A61N 1/3787 |
| 9,106,083 B2 | 8/2015 | Partovi |
| 9,192,704 B2 | 11/2015 | Yomtov et al. |
| 9,302,093 B2* | 4/2016 | Mashiach ............ A61N 1/0551 |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0171792 A1 | 9/2003 | Zarinetchi et al. |
| 2004/0138725 A1 | 7/2004 | Forsell |
| 2004/0256146 A1 | 12/2004 | Frericks |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |

(56) References Cited

U.S. PATENT DOCUMENTS

| | | |
|---|---|---|
| 2008/0027293 A1 | 1/2008 | Vodermayer et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0102639 A1 | 4/2010 | Joannopoulos et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1* | 8/2011 | Janna ............... H01Q 7/02 340/870.31 |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1* | 6/2014 | Scott ............ A61N 1/36139 607/60 |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250703 A1 | 9/2016 | Bornegard |
| 2016/0254704 A1 | 9/2016 | Hansen et al. |

FOREIGN PATENT DOCUMENTS

| | | |
|---|---|---|
| EP | 1513241 A1 | 3/2005 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | WO0074747 A1 | 12/2000 |
| WO | WO0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |

(56) References Cited

FOREIGN PATENT DOCUMENTS

| WO | 2009021220 A1 | 2/2009 |
|---|---|---|
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |
| WO | 2015070202 A2 | 5/2015 |

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

Chargepoint, Inc.;—hargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filed and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

* cited by examiner $$k \approx \frac{A_2}{A_1}$$

$$k \approx \frac{A_2}{A_1} \cos\theta$$

HINGED RESONANT POWER TRANSFER COIL

CROSS-REFERENCE TO RELATED APPLICATIONS

This application is a National Stage application of PCT Application Serial No. PCT/US2014/064959, filed Nov. 11, 2014, which claims the benefit of U.S. Provisional Application No. 61/902,694, filed Nov. 11, 2013, titled "Hinged Resonant Power Transfer Coil", the entire contents and disclosures of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to implantable resonant wireless power transfer systems.

BACKGROUND

Many implantable medical devices require electrical systems to power the implant. Typically, this is achieved using percutaneous wiring to connect a power source to the implant.

More recently, there has been development into powering an implanted device wirelessly with a Transcutaneous Energy Transfer (TET) system, e.g., through an oscillating magnetic field. For a TET system to be useful, electrical energy storage and processing must be provided when external power is interrupted or not available. This electrical energy processing and storage can be implemented with solid-state electronics and a battery.

Typically, implantable medical devices, such as implanted sensors, require very little power to operate. With such low power levels (on the order of milliwatts), power transfer levels and efficiency can be lower. With higher power devices (e.g., on the order of watts and up to 15 W or more), efficient transfer of wireless power is extremely important. Additionally, positions within the body are limited that can accommodate larger implanted devices, some of which are deep below the skin surface. These implant locations require additional attention to position and orientation of both the transmit and receive coils, as well as techniques to improve and maximize transfer efficiency.

Previous TET systems for implantable medical devices required the implanted receiver coil to be positioned just under the skin, and typically include a mechanical feature to align the receive and transmit coils and keep them together. By implanting these devices directly under the skin, the size and power requirements of these implanted devices is limited if they are to be powered by a TET system.

Conventional wireless power transfer systems typically use rigid coils to both transfer and receive wireless power. A rigid coil has the advantage of being easy to manufacture and not placing stress on the wire used in the coil. However, rigid coils cannot be contoured to the shape of a patient, and can therefore be uncomfortable for patients to wear and use.

SUMMARY

A resonator of a wireless power transfer system, comprising a plurality of links connected to another with hinges to form a coil housing, the coil housing being adjustable at the hinges to conform to a body of a patient, and a flexible conductor wire attached to the coil housing, the flexible conductor wire being configured to transmit or receive wireless power.

In some embodiments, the resonator is further configured to bend at the hinges to substantially conform to the anatomy of a patient. In another embodiment, the resonator is configured to conform to an abdomen of the patient. In some embodiments, the resonator is configured to conform to a chest of the patient.

In one embodiment, the flexible conductor wire comprises at least one transmit coil and at least one receive coil. In another embodiment, the flexible conductor layer comprises at least one transmit coil, at least one receive coil, and at least one exciter coil.

In some embodiments, the coil housing comprises silicon. In other embodiments, the coil housing comprises a circular shape. In another embodiment, the coil housing comprises a rectangular shape. In one embodiment, the coil housing comprises an elliptical shape.

In some embodiments, the resonator is bendable into a non-planar configuration.

In one embodiment, the resonator further comprises a locking mechanism configured to lock a preferred position of the coil housing into place.

In another embodiment, the resonator further comprises at least one magnetic shielding element disposed on a portion of the plurality of links. In one embodiment, the at least one magnetic shielding element comprises a ferrite material.

In some embodiments, the flexible conductor wire is disposed on an exterior of the coil housing. In another embodiment, the flexible conductor wire is disposed in an interior of the coil housing. In yet another embodiment, the flexible conductor wire is disposed within a conduit of the coil housing.

A method of transmitting wireless power into a patient is also provided, comprising placing a transmitter coil on a body of the patient, conforming the transmitter coil to the body of the patient, and transmitting wireless power from the transmitter coil to a receiver coil implanted in the patient.

In one embodiment, the conforming step comprises bending a plurality of links of the transmitter coil at hinges of the transmitter coil to adjust a shape of the transmitter coil.

In another embodiment, the method further comprises the step of locking a shape of the transmitter coil after the conforming step.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
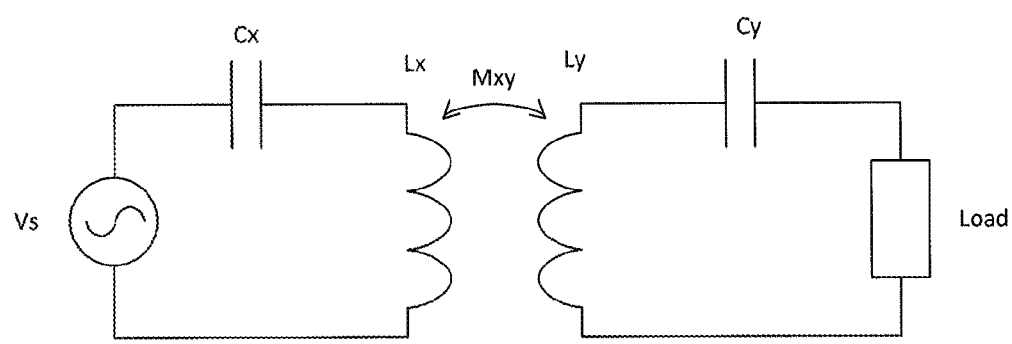
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$M_{xy} = k\sqrt{L_x \cdot L_y}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \text{ μJ}$$

Energy the load removes in one cycle

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 μJ.

The exemplary circuit was analyzed and the self inductance of the receiver coil was found to be 60 uH. From the energy and the inductance, the voltage and current in the resonator could be calculated.

$$e_y = \frac{1}{2} L i^2$$

$$i_y = \sqrt{\frac{2e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \text{ μJ}}{0.05} = 8.4 \text{ mJ}$$

For the same circuit the self inductance of the transmitter coil was 146 uH as mentioned above. This results in:

$$i_x = \sqrt{\frac{2e_x}{L}} = 10.7 \text{ A peak}$$

$$v_x = \omega L_x i_x = 2460 \text{ V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
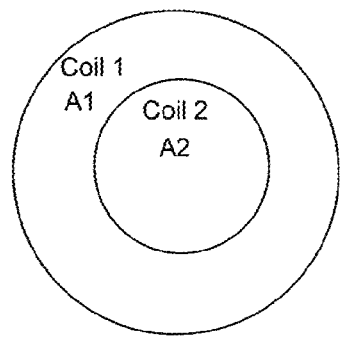
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
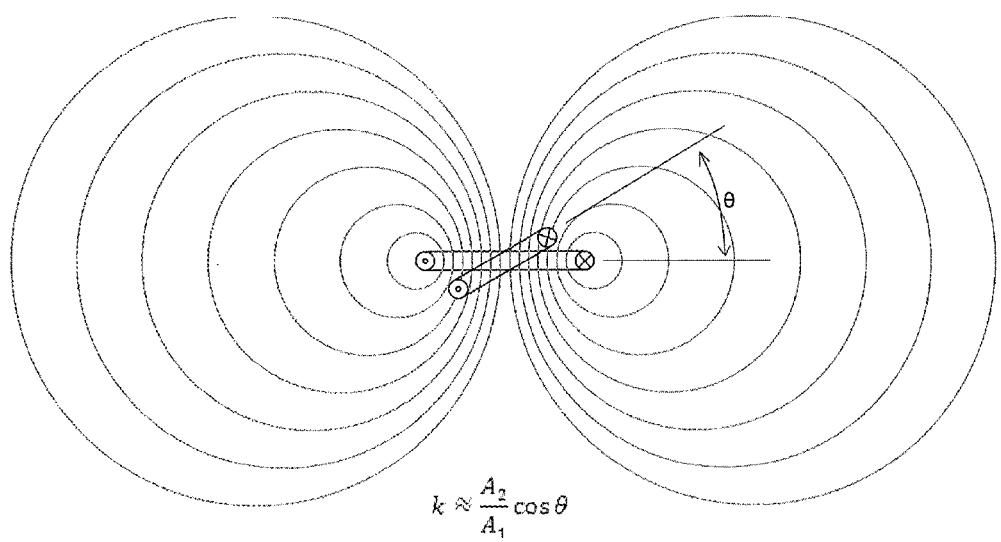
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
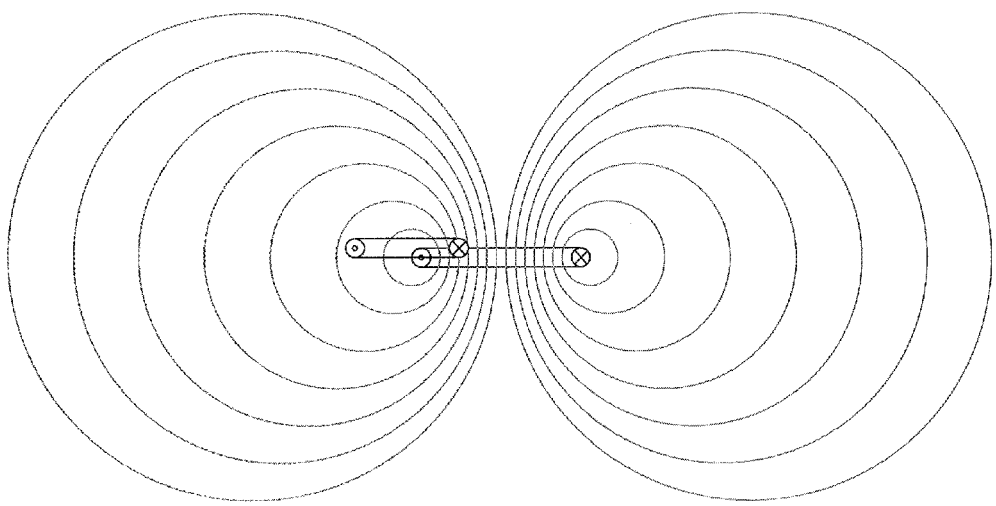

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Transmit and receive coils in conventional wireless power systems typically utilize a rigid, planar design. These rigid and flat coils can be relatively simple to manufacture but come at the expense of being uncomfortable to wear during use, particularly the transmit coils which must be held against the skin to transmit energy into the patient.

In this disclosure, a hinged coil design can be implemented in a TET system to improve patient comfort and convenience during use. The embodiments disclosed herein can apply to either transmit resonator coils or receive resonator coils of a TET system, where non-planar or flexible/adjustable coil designs can advantageously conform to a patient's skin (transmit coil) or to an implantable location within the body (receive coil).

Exemplary Hinted Coil

Figure 4A:
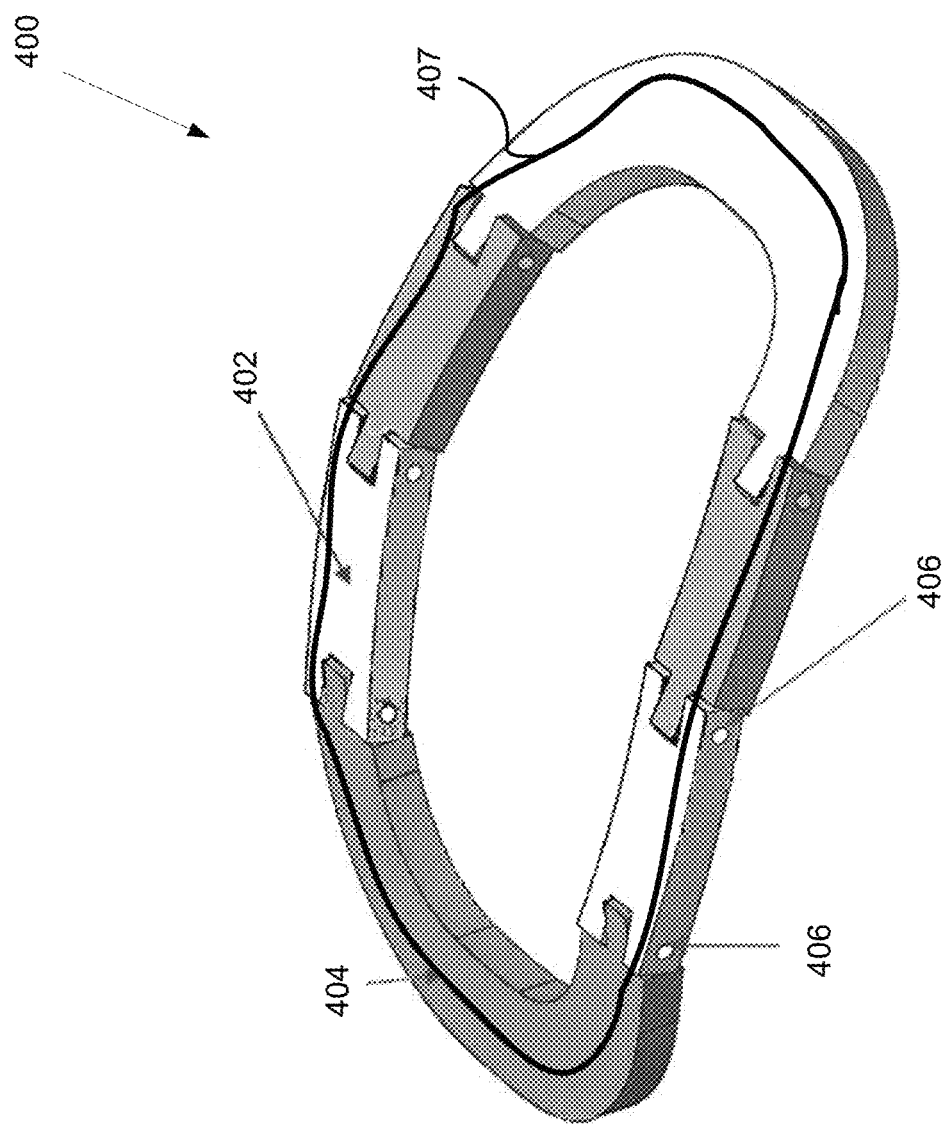
FIGS. 4A-4B illustrate embodiments of an exemplary hinged resonator coil.

FIG. 4A illustrates one embodiment of hinged and/or non-planar resonator coil 400 for use in a TET system. The resonator coil can be a generally oval/elliptical coil, as shown, or alternatively can be a circular coil, a rectangular coil, or square shaped coil, or any other shaped coil. The resonator coil 400 can comprise a plurality of links, such as straight links 402 and curved links 404. In an exemplary embodiment, the links are joined to another with hinges 406.

Figure 4B:
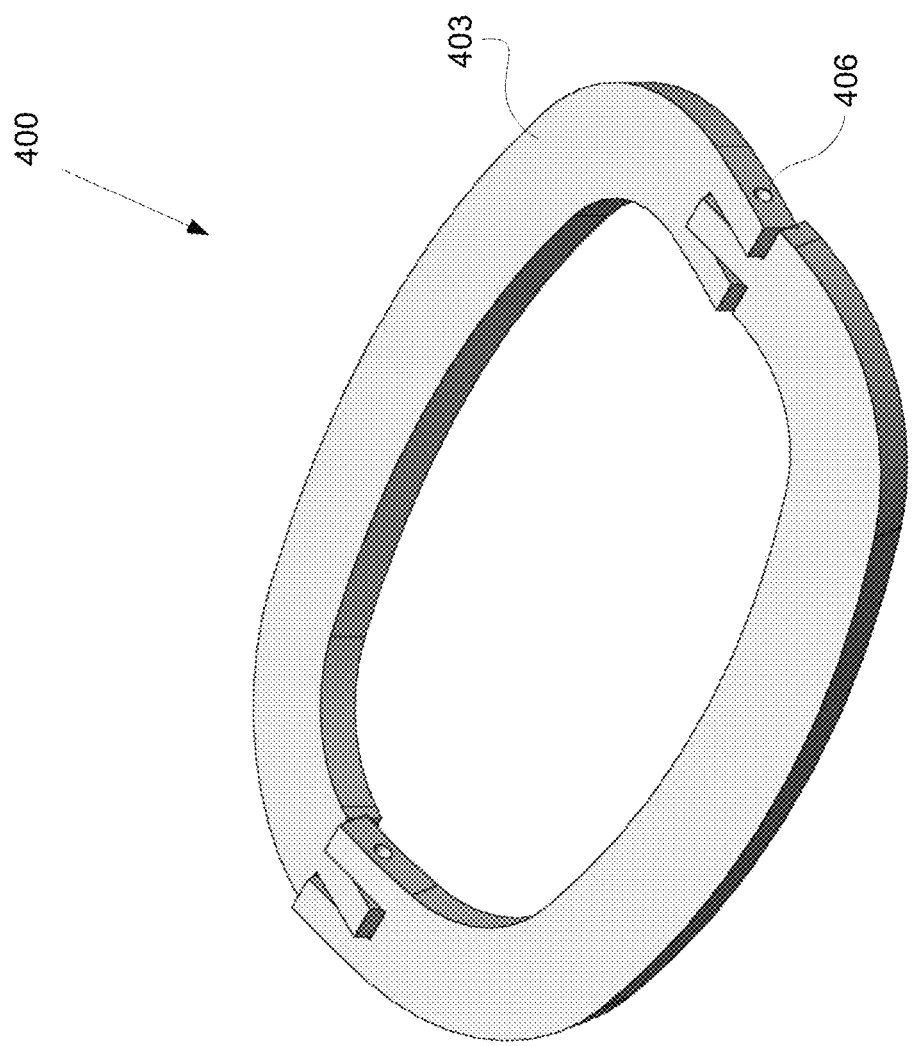

FIG. 4B shows another embodiment of a hinged resonator coil 400. In the embodiment shown, the coil can include only a pair of links 403, joined together by a pair of hinges 406. The simpler, dual hinge configuration shown in FIG. 4B can be desirable for molding or forming to certain parts of a patient's body, such as along a patient's thorax.

Conventional coils for wireless power transfer systems are designed to be rigid. The use of a rigid coil ensures that the interaction between the transmitter and receiver remains consistent. As would be understood by one of skill in the art, non-planar coils can be difficult to tune for effective power transfer. Moreover, changing the shape of the coil will affect the field created by the transmitter coil. For this reason, conventional thought has been to use a rigid, planar coil. The exemplary coil captures the advantages of rigid and flexible coils. The coil can be shaped for the specific application of use, e.g., to fit anatomically to a patient's body. At the same time, the coil can be set to a specific shape during use to enable high performance. Additionally, as described herein, the system includes other features to promote effective coupling and power transfer even when the coil has a non-planar, complex shape.

Although described in terms of a hinged coil, one will appreciate that other configurations may be employed. For example, the relatively rigid links can be joined by elastomeric hinges and barrel hinges. In the case of an elastomeric hinge, the relatively rigid links are joined by an elastomeric material. In one embodiment, the links are joined by a shape memory allow, thermoplastic, or other material to enable shape setting.

Adjacent links can be bent and adjusted to create infinitely adjustable shapes and curvatures in the coil 400. As shown, the embodiments of FIGS. 4A-4B can be adjusted to be non-planar, since portions of the coil resonators bow or bend away from the rest of the coil. In some embodiments the hinges can be configured to hold the coil 400 in a specified shape once the individual links have been bent into a preferred position. In other embodiments, the hinges provide no resistance and can allow the coil to be loosely held together, much like the links of a chain are allowed to sag and bend when not under tension.

In various embodiments, the coil links include a locking mechanism so the preferred position can be locked into place. In one embodiment, the links are connected by hinges having a screw lock. The clinician or patient can conform the coil to the shape of the body, or a comfortable position, when the hinges are in an unlocked position. Thereafter, the hinges can be locked by tightening the screws so the coil shaped is fixed in place. Other types of locking mechanisms may be employed as would be understood by one of skill such as quick locking clamps and barrel locks.

The coil 400 can include a wire or wires 407, such as copper wire, disposed on or within the links. In FIG. 4A, the wire 407 is shown positioned on an exterior of the coil. In other Figures, the wire either isn't shown for ease of illustration, or is disposed within the plurality of links and therefore out of view. The wire can loop in or around each link around the entire coil to create the loop or loops of the resonator coil. In some embodiments, the links can include conduits or tubes to hold the wire(s). In other embodiments, the links can be substantially hollow to allow for room to house the wire(s). Furthermore, the conduits, tubes, or open space of the links allows the wire to extend between the links at the hinges of the coil. In some embodiments, more than one coil can be included in the resonator. For example, a resonator can include any combination of transmit coils, receive coils, and/or exciter coils.

In some embodiments, the coil resonators can be pre-bent or pre-formed to have a particular shape or radius of curvature. For example, if the coil resonator is used as a transmit resonator in a TET system, the coil resonator can be pre-formed at the hinges to conform to a specific portion of a patient's anatomy. This pre-formed shape can vary depending on the specific application or intended position on the patient's body, or depending on where the receive coil is implanted in the patient. For example, a transmit coil configured to be placed on a chest of a patient to access an implanted receive coil near the chest may have less pre-formed curvature than a transmit coil configured to be place on a side or oblique of the patient to access a receive coil implanted in that area of the patient's body. In one embodiment, the pre-shaped coil has non-linear links. The links can have a preformed bend or other shape to promote an improved anatomical fit to a portion of a patient's body. For example, the links may have a slight curvature for wrapping to the oblique or lateral thorax.

In other embodiments, the coil resonator of FIGS. 4A-4B may not have a pre-formed or pre-bent shape, but instead may be adjustable so as to be bent or conformed into any desired shape by the user or by a physician. By designing an adjustable hinged coil for use in a TET system, the individual links of the system can be infinitely customizable and conformable to each unique patient regardless of shape or size. A manufacturer would not need to design an optimal curvature or non-planar coil for each unique application and coil placement, but instead the coils could be easily bent or pressed against a patient's body to perfectly conform to that individual patient's shape. Another advantage of the coil design described herein is that the coil fits to the body shape better than conventional planar coils thereby dramatically improving patient quality of life (QoL).

Figure 4C:
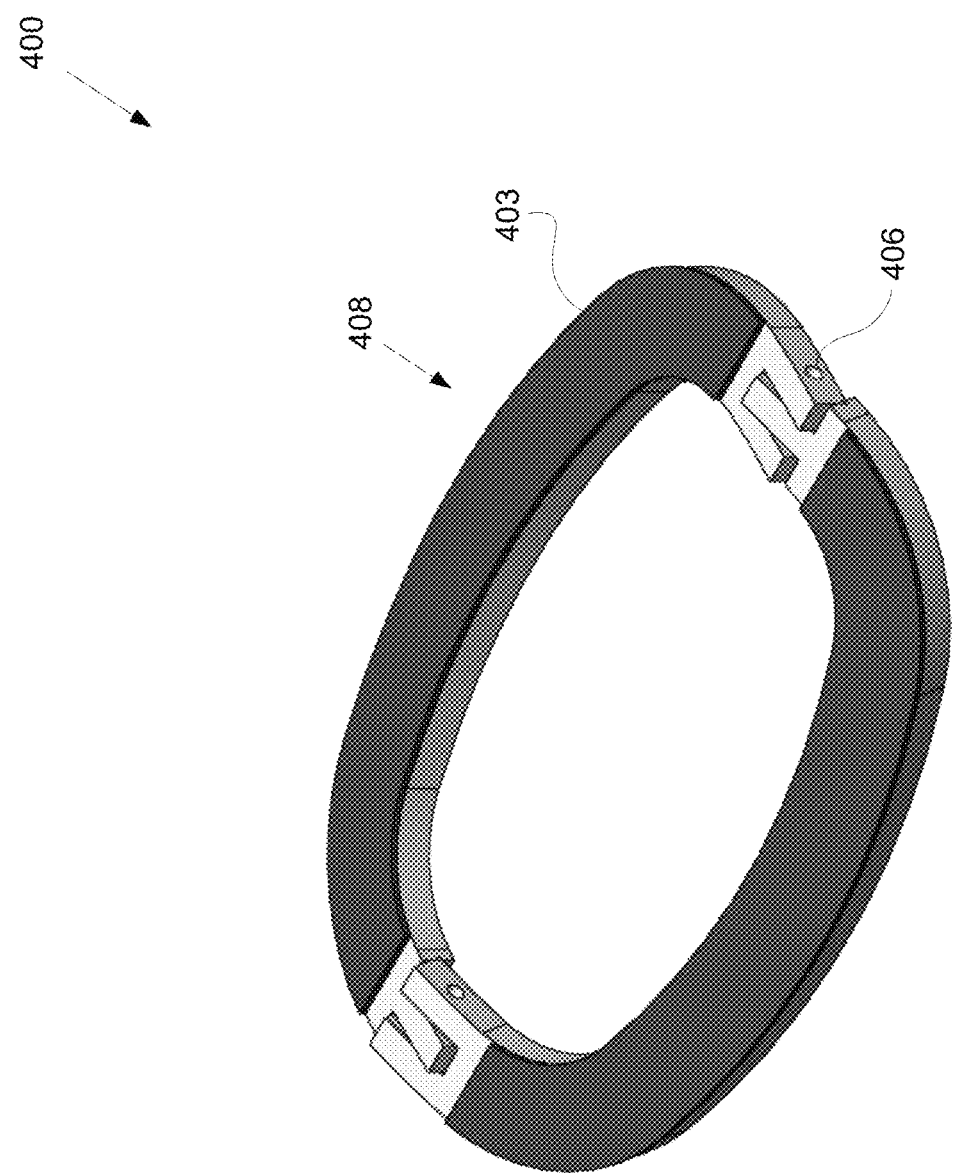
FIGS. 4C-4D show one embodiment of a hinged coil including a ferrite shielding tile.
Figure 4D:
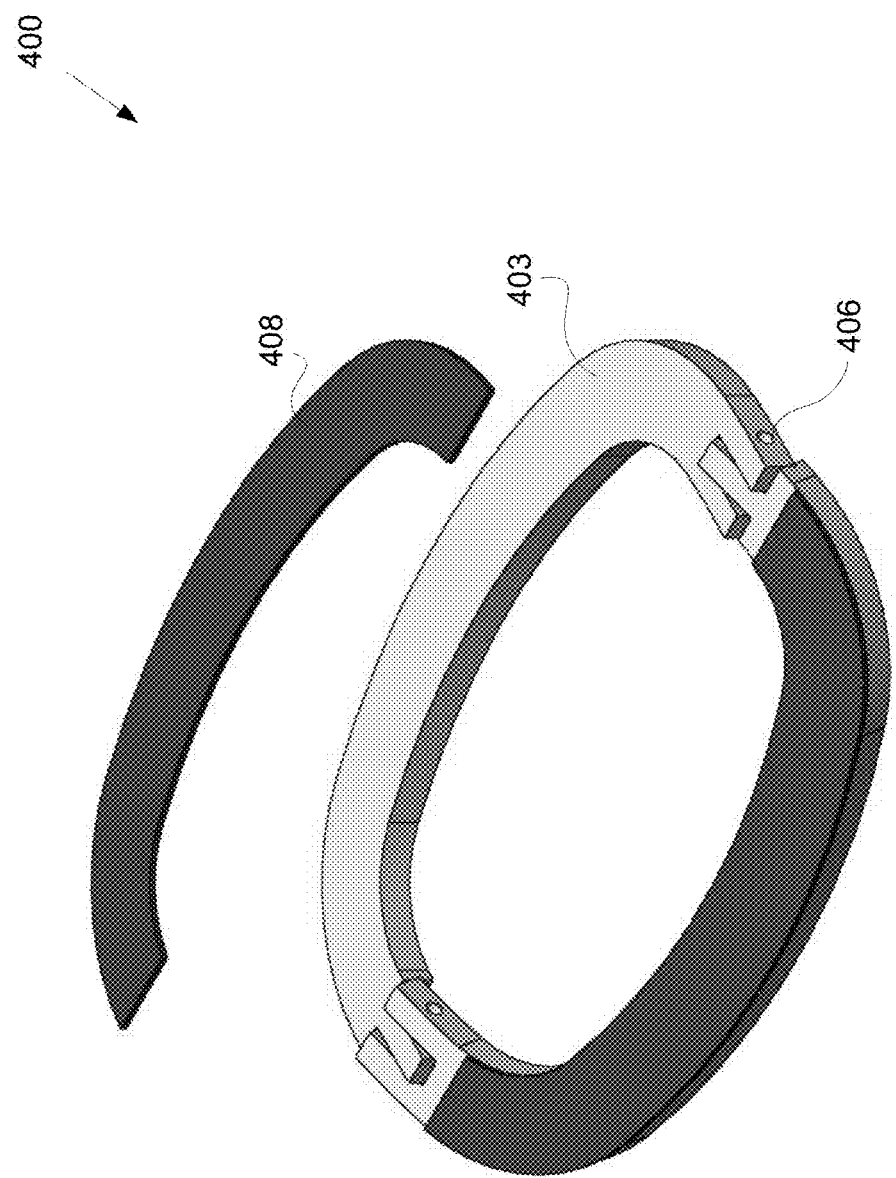

FIGS. 4C-4D show another embodiment of the hinged coil 400 from FIG. 4B. In this embodiment, the coil 400 can further include a magnetic shielding element in the form of ferrite tiles 408 to provide magnetic shielding to the coils. The ferrite tiles 408 can be modular tiles, as shown in FIGS. 4C-4D, which can provide modular shielding to only the hinged components of the coil. FIG. 4C shows the coil 400 with a pair of ferrite tiles 408 disposed on an outer surface of each link 403. FIG. 4D shows a ferrite tile 408 separate from the corresponding link 403. This modular ferrite tile design advantageously adds to durability and manufacturing of the coil 400 due to the brittle nature of ferrite materials.

Figure 5:
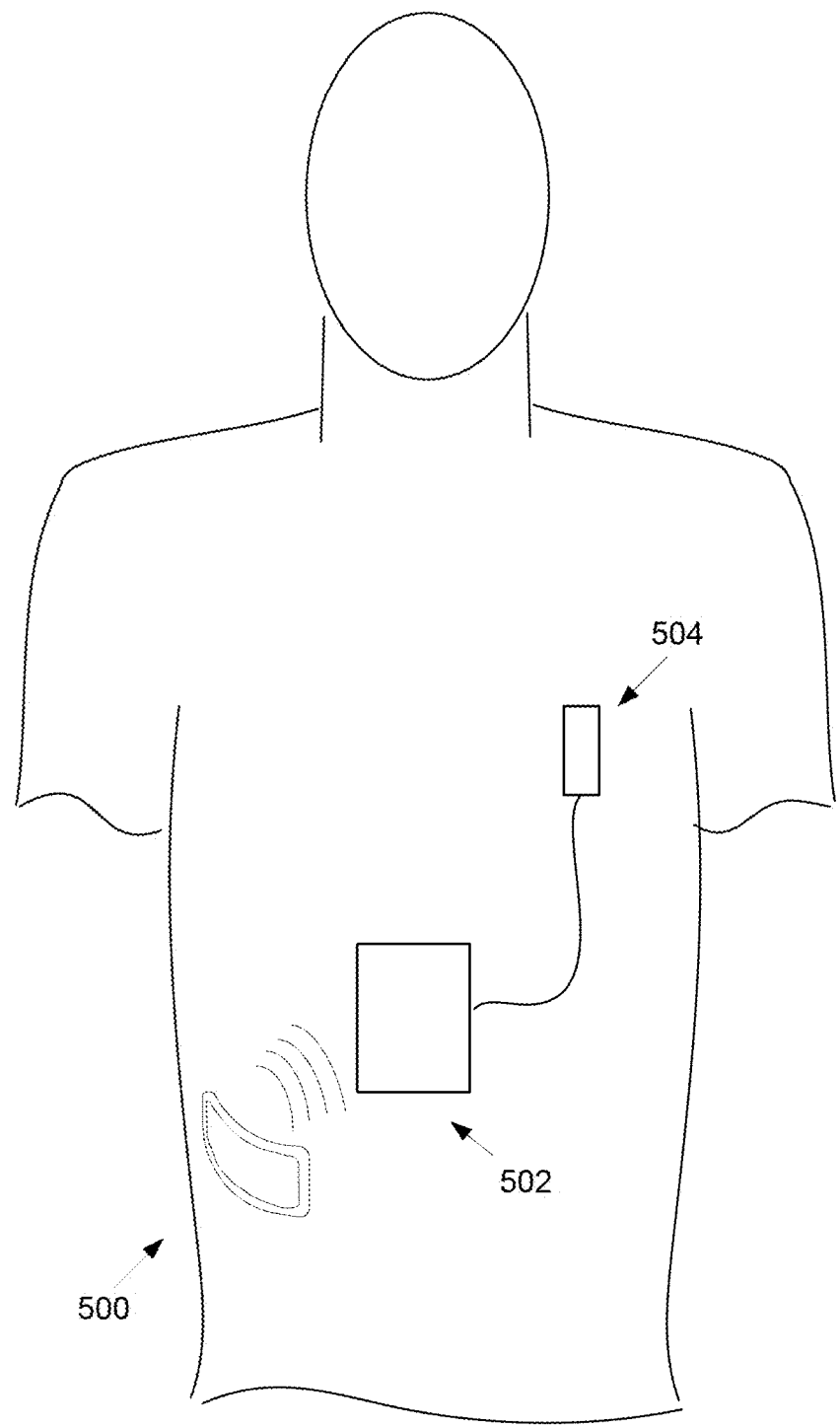
FIG. 5 shows the hinged coil conforming to the body of a patient.

FIG. 5 illustrates one embodiment of a transmit resonator coil 500 positioned on an exterior portion of a patient. In FIG. 5, the transmit coil can be either a pre-bent or pre-shaped resonator coil configured to conform to the anatomy of the patient, or alternatively, the transmit coil can be a hinged or flexible resonator coil configured to be bendable to conform to the anatomy of the patient. The transmit resonator coil 500 can be configured to transmit wireless energy to an implanted receive resonator coil 502 in the patient. In some embodiments, the receive resonator coil can be electrically coupled to an implanted medical device 504, such as a heart pump, to provide energy for the operation of the medical device.

Figure 6:
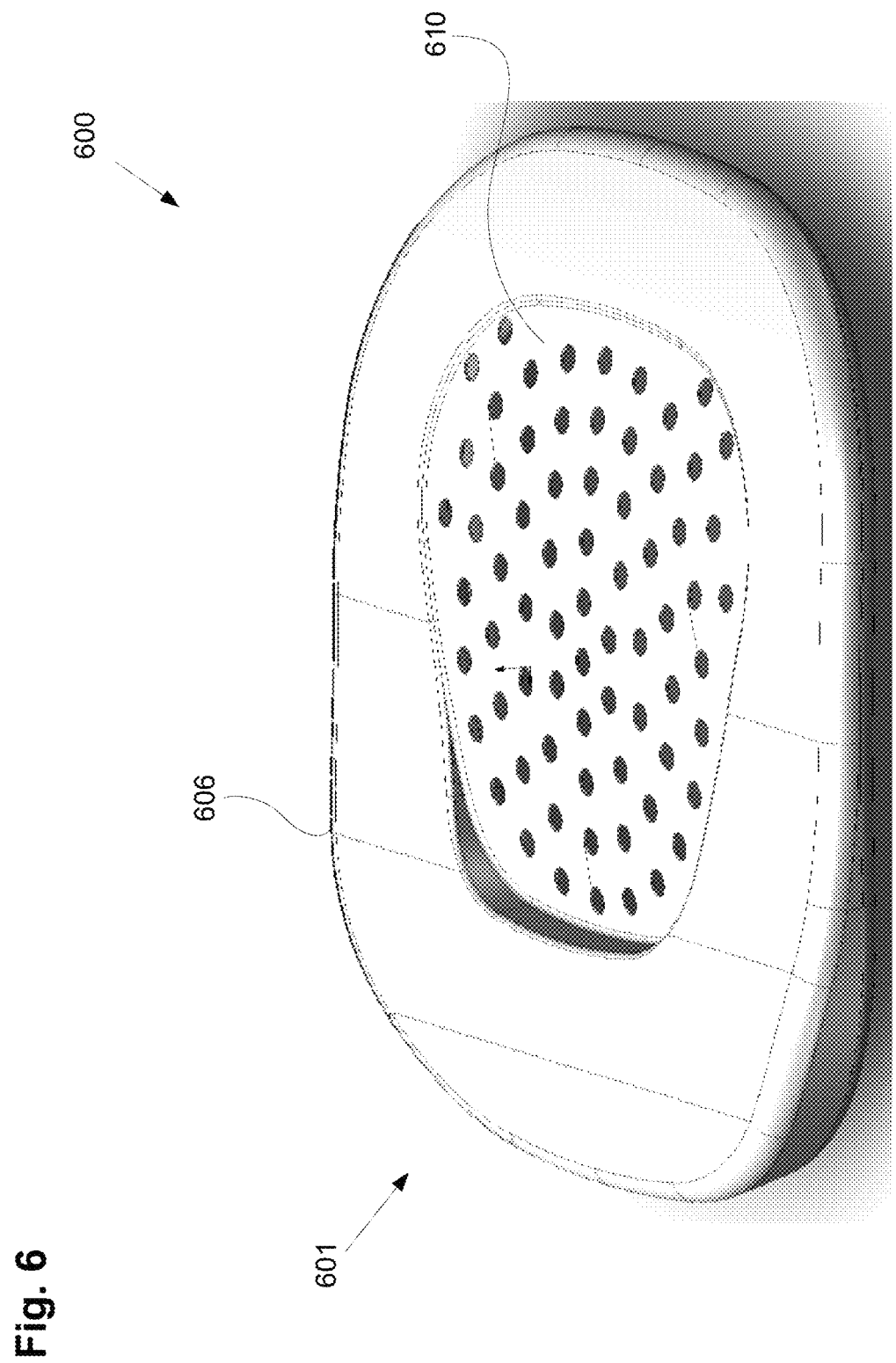
FIG. 6 shows another embodiment of a flexible or hinged coil.

FIG. 6 illustrates yet another embodiment of a hinged or flexible resonant coil 600. In the embodiment shown, the coil can include a flexible or bendable housing 601. The entire housing itself can be bendable or conformable, for example, to allow the coil to be shaped to conform to a patient's body. In another embodiment, the housing can include a number of hinges 606, either internal to the housing 601 or external to the housing to allow for the coil to be shaped as described above. Also shown, the coil 600 can include a central webbed or breathable structure 610 to allow for ventilation of the coil. As described above, the coil 600 can include a number of looped coils of a metal, such as copper, to allow for wireless transmission and reception of power.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A resonator of a wireless power transfer system, comprising:
    a plurality of links connected to another with hinges to form a coil housing, the coil housing being adjustable at the hinges to conform to a body of a patient, wherein the plurality of links are connected end to end to form a closed loop; and
    a flexible conductor wire attached to the coil housing, the flexible conductor wire being configured to transmit or receive wireless power.

2. The resonator of claim 1 being further configured to bend at the hinges to substantially conform to the anatomy of a patient.

3. The resonator of claim 1 wherein the flexible conductor wire extends along the closed loop formed by the plurality of links.

4. The resonator of claim 1 wherein the resonator is configured to conform to a chest of the patient.

5. The resonator of claim 1 wherein the flexible conductor wire comprises at least one transmit coil and at least one receive coil.

6. The resonator of claim 1 wherein the flexible conductor wire comprises at least one transmit coil, at least one receive coil, and at least one exciter coil.

7. The resonator of claim 1 wherein the coil housing comprises silicon.

8. The resonator of claim 1 wherein the coil housing comprises a circular shape.

9. The resonator of claim 1 wherein the coil housing comprises a rectangular shape.

10. The resonator of claim 1 wherein the coil housing comprises an elliptical shape.

11. The resonator of claim 1 wherein the resonator is bendable into a non-planar configuration.

12. The resonator of claim 1 further comprising a locking mechanism configured to lock a preferred position of the coil housing into place.

13. The resonator of claim 1 further comprising at least one magnetic shielding element disposed on a portion of the plurality of links.

14. The resonator of claim 13 wherein the at least one magnetic shielding element comprises a ferrite material.

15. The resonator of claim 1 wherein the flexible conductor wire is disposed on an exterior of the coil housing.

16. The resonator of claim 1 wherein the flexible conductor wire is disposed in an interior of the coil housing.

17. The resonator of claim 16, wherein the flexible conductor wire is disposed within a conduit of the coil housing.

18. A method of transmitting wireless power into a patient, comprising:
    placing a transmitter coil on a body of the patient, the transmitter coil including a plurality of links connected end to end by hinges to form a closed loop;
    conforming the transmitter coil to the body of the patient; and
    transmitting wireless power from the transmitter coil to a receiver coil implanted in the patient.

19. The method of claim 18 wherein the conforming step comprises bending the plurality of links of the transmitter coil at the hinges of the transmitter coil to adjust a shape of the transmitter coil.

20. The method of claim 18 further comprising locking a shape of the transmitter coil after the conforming step.

* * * * *